United States Patent [19]
Hemmerling et al.

[11] Patent Number: 5,384,070
[45] Date of Patent: Jan. 24, 1995

[54] USE OF OPTICALLY ACTIVE TETRAHYDROFURAN-2-CARBOXYLIC ACID ESTERS AS DOPANTS IN LIQUID-CRYSTAL MIXTURES, LIQUID-CRYSTAL MIXTURES CONTAINING SAME AND NOVEL OPTICALLY ACTIVE TETRAHYDROFURAN-2-CARBOXYLIC ACID ESTERS

[75] Inventors: Wolfgang Hemmerling, Sulzbach; Hans-Rolf Dübal, Königstein; Claus Escher, Mühltal; Gerhard Illian, Frankfurt am Main; Yoshio Inoguchi, Tokyo; Ingrid Müller, Hofheim; Mikio Murakami, Königstein; Dieter Ohlendorf, Liederbach; Rainer Wingen, Hattersheim am Main, all of Germany

[73] Assignee: Hoechst Aktiengesellschaft, Frankfurt am Main, Germany

[21] Appl. No.: 65,080

[22] Filed: May 20, 1993

Related U.S. Application Data

[63] Continuation of Ser. No. 884,306, May 11, 1992, abandoned, which is a continuation of Ser. No. 392,344, Aug. 11, 1989, abandoned.

[30] Foreign Application Priority Data

Aug. 13, 1988 [DE] Germany .............................. 3827599

[51] Int. Cl.$^6$ .............................................. C09K 19/34
[52] U.S. Cl. ................................ 252/299.61; 544/318;
544/298; 544/335; 546/268; 546/275; 546/276;
546/277; 546/290; 546/296; 546/301; 546/339;
546/342; 548/128; 548/129; 549/357; 549/473;
549/499; 549/502
[58] Field of Search ........... 252/299.01, 299.6, 299.61,
252/299.63; 544/318, 298, 335; 546/268, 275,
276, 277, 290, 296, 301, 339, 342; 548/128, 129;
549/357, 473, 499, 502

[56] References Cited
U.S. PATENT DOCUMENTS 4,873,019 10/1989 Krause et al. ................... 252/299.61

OTHER PUBLICATIONS

Chemical Abstracts, vol. 103, No. 46 339r.
Chemical Abstracts, vol. 103(3), No. 22 510m (Jul. 22, 1985).
Chemical Abstracts, vol. 109(16), No. 139 802a (Oct. 17, 1988).
Chemical Abstracts, vol. 94(24), No. 200 881r (Jun. 15, 1981).
Chemical Abstracts, vol. 103(6), No. 46 339r (Aug. 12, 1985).
Chemical Abstracts, vol. 104, No. 99 976y (1986).
J. W. Goodby et al., "Ferroelectric Liquid Crystals", pp. 133 and 244 (Philadelphia, 1991).

*Primary Examiner*—Philip Tucker
*Attorney, Agent, or Firm*—Curtis, Morris & Safford

[57] ABSTRACT

The use of optically active tetrahydrofuran-2-carboxylic acid esters as dopants in liquid-crystal mixtures, liquid-crystal mixtures containing same and novel optically active tetrahydrofuran-2-carboxylic acid esters.

Optically active tetrahydrofuran-2-carboxylic acid esters containing a mesogenic molecular building unit are suitable as dopants in liquid-crystal mixtures. They result in liquid-crystalline ferroelectric phases having short switching times and in electroclinic phases having large electroclinic coefficients. A further advantage is that they induce a helix having a very small pitch so that they are also suitable for helix compensation in LC mixtures.

The compounds are symbolized by the general formula:

$$R^1(-A^1)_j(-M^1)_k(-A^2)_l(-M^2)_m(-A^3)_n-X-\underset{O}{\overset{}{C}}\overset{*}{\underset{}{\diagdown}}\hspace{-2pt}\begin{array}{c}\diagup\\O\end{array}$$

in which the symbols and indices essentially denote:
$R^1$=alkyl/alkenyl or tetrahydrofurancarbonyloxy or -thio; j, l, n=zero, 1 or 2; k, m=zero or 1; $-A^1$, $-A^2$, $-A^3$=phenylene, cycloalkylene or corresponding heterocyclates containing nitrogen, oxygen or sulfur; $-M^1$, $-M^2$=bridges such as $-CO-O$, $-OCH_2$ or $-CH=CH$; X=oxygen or sulfur.

5 Claims, No Drawings

USE OF OPTICALLY ACTIVE TETRAHYDROFURAN-2-CARBOXYLIC ACID ESTERS AS DOPANTS IN LIQUID-CRYSTAL MIXTURES, LIQUID-CRYSTAL MIXTURES CONTAINING SAME AND NOVEL OPTICALLY ACTIVE TETRAHYDROFURAN-2-CARBOXYLIC ACID ESTERS

This application is a continuation of application Ser. No. 07/884,306, filed May 11, 1992, now abandoned which is a continuation of Ser. No. 07/392,344, filed Aug. 11, 1989, now abandoned.

The use of optically active tetrahydrofuran-2-carboxylic acid esters as dopants in liquid-crystal mixtures, liquid-crystal mixtures containing same and novel optically active tetrahydrofuran-2-carboxylic acid esters.

In the last decade particularly, liquid crystals have found their way into various technical fields in which electro-optic and display device properties are required (for example, in clock, pocket-calculator and typewriter displays). These display devices are based on the dielectric alignment effects in the nematic, cholesteric and/or smectic phases of the liquid-crystalline compounds, in which—due to the dielectric anisotropy—the long molecular axis of the compounds assumes a preferred alignment in an applied electric field. For many other potential fields of application of liquid crystals, which are per se very promising chemical compounds for technology owing to their unique properties, the normal switching times in these display devices tend to be too long. This disadvantage manifests itself, in particular, if a large number of image points has to be driven, as a result of which the production costs of appliances which contain fairly large areas, for example video recorders, oscillographs or television, radar, EDP or automatic printer display screens, become too high.

In addition to the nematic and cholesteric liquid crystals, optically active smectic liquid crystal phases have been gaining in importance for some years to an increasing extent.

Clark and Lagerwall were able to show that the use of ferroelectric liquid-crystal systems in very thin cells results in opto-electric switching and display components which, compared with the conventional TN ("twisted nematic") cells have switching times which are faster by a factor of 1,000 (cf. for example, Lagerwall et al. "Ferroelectric Liquid Crystals for Displays", SID Symposium, October Meeting 1985, San Diego, Calif., USA). Owing to these and other favorable properties, for example the bistable switching facility and the contrast which is virtually independent of viewing angle, FLCs are in principle well suited for the abovementioned fields of application, for example using a matrix drive.

Another electro-optic effect, which is termed the electroclinic effect, is exhibited by orthogonal chiral smectic phases, for example $S^*_A$, $S^*_B$, $S^*_E$. This effect (S. Garoff et al., Phys. Rev. Lett. 38, 848 (1977)) is a field-induced tilting of the molecules whose angle of tilt $\theta$ varies in proportion to the applied field. The molecules of the orthogonal phases are therefore able to follow the change in field continuously, and they are able to follow, in particular, an alternating field up to a cutoff frequency $f_G$, whereas ferroelectric systems always change and retain their angle of tilt abruptly on reaching a particular field strength until a corresponding field of opposite direction is applied (bistable switching).

Both effects, the ferroelectric and the electroclinic, can be exploited in constructing electro-optic switching and display components in accordance with their specific properties. For this purpose, it is either necessary to have compounds which form tilted or orthogonal smectic phases and are themselves optically active or to be able to induce ferroelectric or electroclinic smectic phases by doping compounds which, although they form such smectic phases, are not themselves optically active, with optically active compounds. At the same time the desired phase should be stable over as large a temperature range as possible.

To achieve a good contrast ratio in electro-optic components, a uniform planar orientation of the liquid crystals is necessary. A good orientation in the $S^*_A$ and $S^*_C$ phase can be achieved if the phase sequence of the liquid-crystal mixture with decreasing temperature is as follows:

$$\text{Isotropic} \rightarrow N^* \rightarrow S^*_A \rightarrow S^*_C.$$

A requirement is that the pitch (pitch of the helix) in the N* phase is very large (larger than 10 μm) or still better is completely compensated for (T. Matsumoto et al., pages 468–470, Proc. of the 6th Int. Display Research Conf., Japan Display, Sep. 30–Oct. 2, 1986, Tokyo, Japan; M. Murakami et al., ibid., pages 344–347). This is achieved by adding, to the chiral liquid-crystal mixture which has, for example, a levorotatory helix in the N* phase, a further optically active dopant which induces a dextrorotatory helix, in such amounts that the helix is precisely compensated for.

It has now been found that optically active tetrahydrofuran-2-carboxylic acid esters as dopants in tilted smectic liquid-crystal phases result in short switching times and, in orthogonal smectic liquid-crystal phases, in high electroclinic coefficients, even if small amounts are added. The helix induced by the tetrahydrofuran-2-carboxylic acid esters in the N* phase may advantageously be used in mixtures to compensate for the pitch in a controlled manner.

The invention therefore relates to the use of optically active tetrahydrofuran-2-carboxylic acid esters as dopants in liquid-crystal mixtures. The invention furthermore relates to liquid-crystal systems which contain optically active tetrahydrofuran-2-carboxylic acid esters and also novel optically active tetrahydrofuran-2-carboxylic acid esters. The tetrahydrofuran-2-carboxylic acid esters to be used according to the invention correspond to the general formula (I)

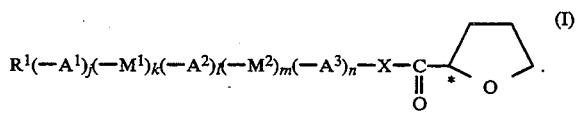

$$R^1(-A^1)_l(-M^1)_k(-A^2)_l(-M^2)_m(-A^3)_n-X-\underset{\underset{O}{\|}}{C}-\text{\scriptsize{(I)}}$$

in which the symbols and indices have the following meaning:

\* indicates an optically active carbon atom, $R^1$ is

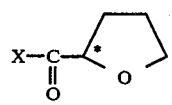

or a straight-chain or branched alkyl radical containing 1 to 16 carbon atoms or a straight-chain or branched alkenyl radical containing 3 to 16 carbon atoms, it being possible for these radicals themselves to contain asymmetric carbon atoms, for one or more nonadjacent —$CH_2$— groups to be replaced by —O—, —S—, —CO—, —O—CO— and/or —CO—O—, and for one or more hydrogen atoms to be replaced by fluorine, chlorine, bromine or CN, j and l are zero, 1 or 2, k and m are zero or 1, n is zero, 1 or 2, with the following proviso: if j and/or l=zero, k=zero; if n=zero, m=zero; the sum of j+l+n is not less than 1 and not more than 3, —$A^1$, —$A^2$ is

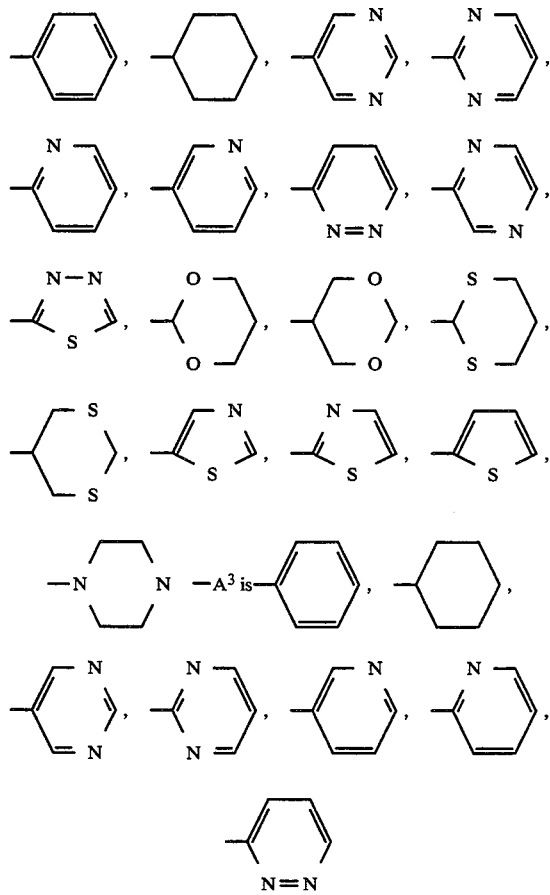

—$M^1$, —$M^2$ is —CO—O, —O—CO, —$CH_2CH_2$—, —CH=CH—, —$CH_2$O, —O$CH_2$ and

X is O or S.

In a preferred embodiment, the symbols in the general formula (I) have the following meaning:

$R^1$ is a straight-chain or branched alkyl or alkenyl radical containing 4 to 14 carbon atoms which may contain an asymmetric carbon atom, or it being possible for a —$CH_2$— group to be replaced by —O—, —CO— or —CO—O—, or for one or more hydrogen atoms to be replaced by fluorine, j and l are zero or 1, k, m, n are zero or 1.

In a further preferred embodiment, use is made of tetrahydrofuran-2-carboxylic acid esters of the general formula (IV):

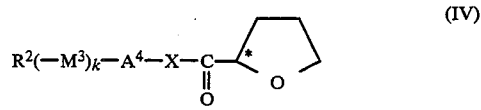     (IV)

in which:

$R^2$ denotes a straight-chain or branched alkyl or alkenyl radical containing 6 to 12 carbon atoms, which may contain an asymmetric carbon atom;

—$M^3$ denotes —O, —S, —O—CO or —CO

—$A^4$ denotes

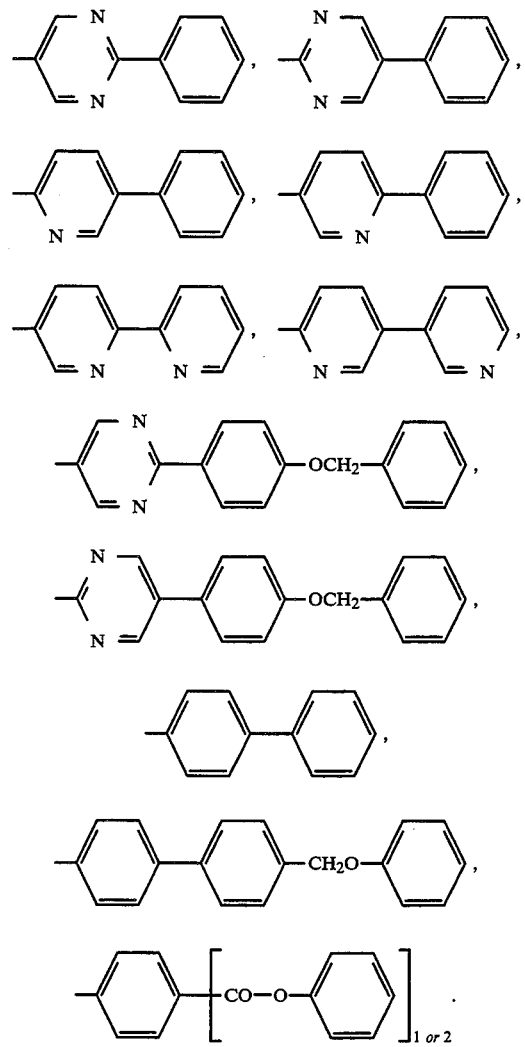

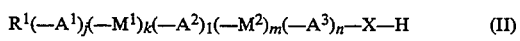

To prepare the compounds of the general formula (I) mesogenic phenols or thiophenols of the general formula (II):

$R^1$(—$A^1$)$_j$(—$M^1$)$_k$(—$A^2$)$_l$(—$M^2$)$_m$(—$A^3$)$_n$—X—H     (II)

are reacted with derivatives of tetrahydrofuran-2-carboxylic acid of the formula (III):

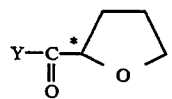
(III)

where Y denotes an OH group or halogen. For Y=OH, the esterification with (II) is carried out in the presence of Bronsted or Lewis acids, possibly in the presence of hydrophylic agents, or with condensation reagents such as N, N'-carbonyldiimidazole, dicyclohexylcarbodiimide or azodicarboxylic acid ester/triphenylphosphine. For Y= halogen, the reaction with (II) is carried out in the presence of acid scavengers, in particular pyridine or triethylamine. Finally, the alkali-metal or alkaline earth salts (II) may also be reacted with the acid halides [(III) with Y=halogen] to form (I). The reaction product may be purified by measures known per se, for example recrystallization or crystallographic separation methods.

Phenolic or thiophenolic substances of the formula (II) are known. The methods of preparing optically active tetrahydrofuran-2-carboxylic acids are also known [for example P. C. Belander et al., Can. J. Chem. 61, 1383 (1983); H. B. Kagan et al., in "Topics in Stereochemistry" (edited by E. L. Eliel and S. H. Wilen), Vol. 18, pages 249. et seq, Wiley Interscience, New York, Chichester, Brisbane, Toronto, Singapore, 1988].

The liquid-crystal mixtures according to the invention form liquid-crystal phases and contain at least one optically active tetrahydrofuran-2-carboxylic acid ester.

The term "liquid-crystal phase" is understood to mean nematic, cholesteric, orthogonal smectic or tilted smectic, in particular $S*_2$, $S*_B$ and $S*_C$ phases. The liquid-crystal mixtures are composed of 2 to 20, preferably 2 to 15 components, including at least one of the chiral compounds claimed according to the invention.

The other constituents are preferably selected from the known compounds having nematic, cholesteric and/or smectic, for example $S_A$ phases, and/or tilted smectic phases; these include, for example, Schiff's bases, biphenyls, terphenyls, phenylcyclohexanes, cyclohexylbiphenyls, N-, S- or O-containing heterocyclics (for example pyrimidines), cinnamic acid esters, cholesterol esters, and various bridged, terminally polar polynuclear esters of p-alkylbenzoic acids. In general, the liquid-crystal mixtures available commercially already exist, before the optically active compound(s) is added, as mixtures of a wide range of components, of which at least one is mesogenic, i.e. as a compound which, in the form of a derivative or mixed with certain associated components, exhibits a liquid-crystal phase which makes it possible to expect the formation of an enantiotropic (clearing point>melting point) or monotropic (clearing point<melting point) mesophase.

The liquid-crystal mixtures contain in general 0.05 to 70% by weight, in particular 0.1 to 50% by weight, of the compound(s) according to the invention.

The compounds according to the invention are suitable, in particular as dopants for tilted smectic liquid-crystal phases since they convert them into ferroelectric liquid-crystal phases; the values of the spontaneous polarization ($P_s$) are in the region of about 15–35 nC cm$^2$ for 10 mol % doping and at 25° C. and in the region of about 150–350 nC/cm$^2$ when linearly extrapolated to the pure compound; in some cases, the values of $P_s$ are even higher still. The switching times of the novel systems are frequently below 100 μs for 10 mol % doping, at 25° C. and with a switching voltage of ±10 V/μm. The compounds according to the invention may also be used to achieve the electroclinic effect in orthogonal smectic phases ($S*_A$, $S*_B$, $S*_E$).

EXAMPLE 1

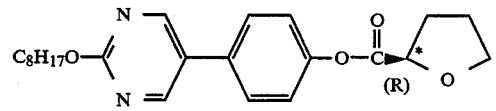

4-(2-n-Octyloxy-5-pyrimidinyl)phenyl (R)-tetrahydrofuran-2-carboxylate 901 mg (3 mmol) of 4-(2-n-octyloxy-5-pyrimidinyl)-phenol, 464.5 mg (4 mmol) of (R)tetrahydrofuran-2-carboxylic acid and also 49 mg (0.4 mmol) of 4-dimethylaminopyridine are added at room temperature to a solution of 825 mg (4 mmol) of dicyclohexylcarbodiimide in 20 ml of dry dichloromethane while stirring. After stirring for 10 hours at room temperature, the reaction solution is evaporated down in vacuo. Chromatographic purification and recrystallization from n-hexane yield 710 mg (59%) of colorless crystals with $[\alpha]_D^{25} = -8.8°$ (c=2, CHCl$_3$).

Melting point: 75° C.

The following are obtained analogously:

EXAMPLE 2

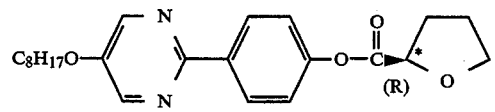

4-(5-n-Octyloxy-2-pyrimidinyl)phenyl (R)-tetrahydrofuran-2-carboxylate $[\alpha]_D = 9.2°$ (c=2, CHCl$_3$) Melting point: 90° C.

EXAMPLE 3

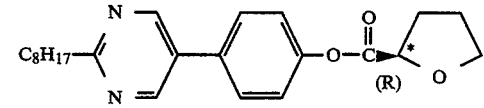

4- (2-n-Octyl-5-pyrimidinyl)phenyl (R)-tetrahydrofuran-2-carboxylate $[\alpha]_D = -9.3°$ (c=2, CHCl$_3$) Melting point: 68° C.

EXAMPLE 4

4-(5-n-Octyl-2-pyrimidinyl)phenyl (R)-tetrahydrofuran-2-carboxylate

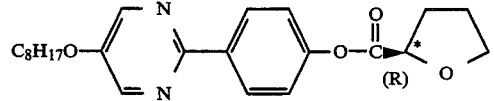

$[\alpha]_D = -9.8°$ (c=2, CHCl$_3$) Melting point: 74° C.

EXAMPLE 5

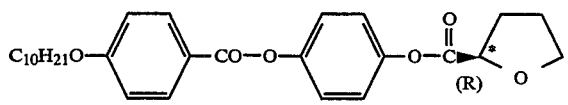

4-(4-n-decyloxybenzoyl)phenyl (R)-tetrahydrofuran-2-carboxylate $[\alpha]_D = -6.1°$ (C=2, CHCl$_3$) Melting point: 80° C.

EXAMPLE 6

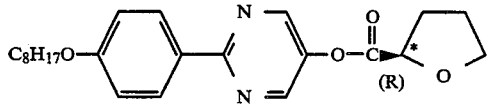

2-(4-n-octyloxyphenyl)-5-pyrimidinyl (R)-tetrahydrofuran-2-carboxylate $[\alpha]_D = -8.2°$ (c=2, CHCl$_3$) Melting point: 90° C.

EXAMPLE 7

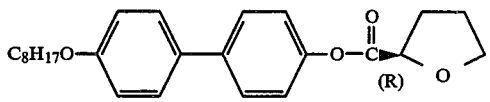

4-n-Octyloxybiphenyl-4-yl (R)-tetrahydrofuran-2-carboxylate $[\alpha]_D = -9.4°$ (c=2, CHCl$_3$) Melting point: 119° C.

EXAMPLE 8

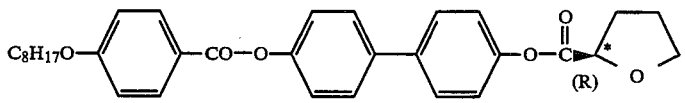

4-(4-n-Octyloxybenzoyloxy)biphenyl-4'-yl (R)-tetrahydrofuran-2-carboxylate $[\alpha]_D = -6.9°$ (c=2, CHCl$_3$) Phase sequence: K 121 (105 S*$_x$106 S*$_C$116) N* 195 I Melting point: 73° C.

EXAMPLE 9

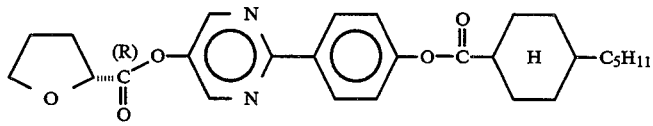

2-[(trans-4-pentylcyclohexyl)carhonyloxyphenyl]-5-pyrimidinyl (R)-tetrahydrofuran-2-carboxylate $[\alpha]_D^{25} = -3.08°$ (c=2, CHCl$_3$) Melting point: 153; clearing point: 206

EXAMPLE 10

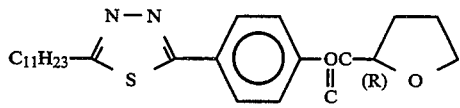

4-(5-n-Undecyl-1,3,4-thiadiazol-2-yl)phenyl (R)-tetrahydrofuran-2-carboxylate $[\alpha]_D^{25} = -9.88°$ (c=2, CHCl$_3$) Phase sequence: K 91 I

EXAMPLE 11

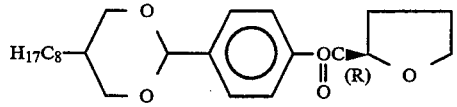

4-(5-n-octyl-1,3-dioxan-2-yl)phenyl (R)-tetrahydrofuran-2-carboxylate $[\alpha]_D^{25} = -5.16°$ (c=CHCl$_3$) Phase sequence: K 94 I

Application examples A1 to A7

To check the effectiveness of the compounds described above as ferroelectric dopants in liquid-crystal systems having tilted smectic phases, they are mixed in a concentration of 10 mol % in each case with a nonchiral basic mixture (A) having the phase sequence:

K 12.5 S$_c$ 83 S$_A$ 95 N 100 I.     (A)

In each case the values of the spontaneous polarization (P$_s$ in nC/cm$^2$), of the switching time $\tau$ (in μs) and of the optical angle of tilt of the S$_C$ phase $\theta$ (in °) of the mixture were determined. The P$_s$ values are measured by the method of H. Diamant et al. (Rev. Sci. Instr., 28, 30, 1957). With a cell layer thickness of approx. 2 μm uniform planar orientation of the liquid crystals in the S*$_C$ phase is achieved by orientation layers [SSFLC Technik, Clark et al., Appl. Phys. Lett. 36, 899 (1980)]. To determine $\tau$ and $\theta$, the measuring cell is mounted on the revolving stage of a polarizing microscope between crossed analyser and polarizer. The switching angle 2$\theta$ is measured with a static electric field applied to the measuring cell. For positive and negative polarity of this field, the measuring cell is rotated in each case until minimum light transmission occurs. The difference in angle between the two orientations so determined yields the switching angle. The switching time $\tau$ is determined with the acid of a photodiode by measuring the rise time of the light signal from 10 to 90% signal amplitude. The switching voltage is ±10 V/μm. In addition to the values of P$_s$, $\tau$ and 2$\theta$, the S*$_C$ range of the respective mixture is specified; in this connection, the values in brackets indicate the supercoolable lower temperature limit of the S$_C$ range.

The pitch Z and the twisting force HTP in the cholesteric phase were determined as described by P. Kassubek et al., Mol. Cryst. Liq. Cryst., Vol. 8, page 305 to 314, 1969, in a wedge-shaped cell having an orientation layer by measuring the displacement lines under the polarizing microscope.

Method of measurement: If a small amount of a chiral compound is added to a (nonchiral) solvent, the plane of the linearly polarized light is rotated through the (characteristic) angle α; this angle is specified as follows: $[α]_D^T$ (c=x, LM), the symbols having the following meaning: x=concentration of the solution in g/l, LM=solvent, D=589 nm (NaD line), T=temperature of the solution. The angle of rotation is determined in a polarimeter after the light has passed through 10 cm.

Table 1 summarizes the result.

TABLE 1

| Application example | (Substance) example | $S_c*$ range in mixture (A)/°C. | $P_s^{(1)}$ nC/cm$^2$ | $τ^{(1)}$ μs | $2θ^{(1)}$ deg. | HTP$^{(2)}$ μm$^{-1}$ |
|---|---|---|---|---|---|---|
| A 1 | 1 | [−8] 12–77 | 16 | 100 | 27 | 3 |
| A 2 | 2 | [−6] 14–77.5 | 17 | 15 | 25 | 1.5 |
| A 3 | 3 | [−9] 27–71 | 16 | 115 | 26 | 3.5 |
| A 4 | 4 | [−11] 10–66 | 35 | 60 | 26 | 1.9$^{(4)}$ |
| A 5 | 6 | [−10] 14–76 | 15 | 120 | 31 | 1.6 |
| A 6 | 7 | [−2] 15–80 | 10$^{(3)}$ | 40$^{(3)}$ | 24$^{(3)}$ | 1.8 |
| A 7 | 8 | [0] 15–83 | 4$^{(3)}$ | 95$^{(3)}$ | 22$^{(3)}$ | 0.1 |

$^{(1)}$Measured values at 25° C.
$^{(2)}$Measured values at 95° C.
$^{(3)}$Measured values at 50° C.
$^{(4)}$Measured values at 85° C.

Application Example A8

A ferroelectric mixture containing the components

| | |
|---|---|
| liquid-crystalline basic mixture A | 90 mol % |
| 4-(2-n-octyloxy-5-pyrimidinyl)phenyl (R)-tetrahydrofuran-2-carboxylate | 5.93 mol % |
| (2S, 3R)-2-[4-(5-octyl-2-pyrimidinyl)-phenyloxy]methyl-3-butyloxirane | 3.38 mol % | has the following liquid-crystalline phase ranges:

X 5 S*$_C$ 72.5 S*$_A$ 87 N* 98 I.

At 25° C., this mixture has a spontaneous polarization of 23 nC/cm$^2$, and a switching time of 42 μs with a switching field of 10 V/μm. The melting point of this mixture is 7° C. below the melting point of the basic mixture A. The pitch of this mixture is greater than 21 μm at 90° C.

Application example A9

A ferroelectric mixture is composed of the components

| | |
|---|---|
| Basic mixture A | 90 mol % |
| 2-(4'-dodecyloxyphenyl)-5-pyrimdinyl (R)-2,2-dimethyl-1,3-dioxolane-4-carboxylate | 6.07 mol % |
| 4-(2-n-octyloxy-5-pyrimidinyl)phenyl (R)-tetrahydrofuran-2-carboxylate | 3.93 mol % | and has the following liquid-crystalline phase ranges:

X 7.4 S* 81 S* 86 N* 100 I.

At 25° C., this mixture has a spontaneous polarization of 18 nC/cm$^2$, and a switching time of 51 μs with a switching field of 10 V/μm. The melting point of this mixture is 5.5° C. below that of the basic mixture A. The pitch of this mixture is greater than 40 μm at a temperature of 90° C.

From the application examples A8 and A9 it is evident that, even in combination with other dopants, the tetrahydrofuran derivatives result in very good ferroelectric mixtures which, owing to the large pitch, can be satisfactorily oriented and have short switching times.

Application Example A10

A ferroelectric liquid-crystalline mixture composed of

| | |
|---|---|
| 5-octyloxy-2-(4-hexyloxyphenyl)pyrimidine | 12.5 mol % |
| 5-octyloxy-2-(4-octyloxyphenyl)pyrimidine | 4.1 mol % |
| 5-octyloxy-2-(4-butyloxyphenyl)pyrimidine | 13.9% |
| 5-octyloxy-2-(4-decyloxyphenyl)pyrimidine | 7.6 mol % |
| 5-octyloxy-2-(4-dodecyloxyphenyl)pyrimidine | 7.6 mol % |
| 5-octyloxy-2-(4-dodecylphenyl)pyrimidine | 11.2 mol % |
| 4-(5-decyl-2-pyrimidinyl)phenyl trans-4-pentylcyclohexanecarboxylate | 17.75 mol % |
| 4-(5-octyl-2-pyrimidinyl)phenyl hexancarboxylate | 4.1 mol % |
| 4-(nonyloxy-5-pyrimidinyl)phenyl 2-chloro-4-methylpentanoate (racemate) | 4.1 mol % |
| (R)-4-(5-n-octyloxy-2-pyrimidinyl)phenyl (2,2-pentamethylene-1,3-dioxolan-4-yl)methyl ether | 4.5 mol % |
| 4-(2-octyloxy-5-pyrimidinyl)phenyl (2R,3R)-3-propyloxirane-2-carboxylate and | 4.35 mol % |
| 4-(5-n-octyl-2-pyrimidinyl)phenyl (R)-tetrahydrofuran-2-carboxylate | 8.3 mol % | has the following phase ranges:

X−8 S*$_C$ 66 S*$_A$ 73 N* 81 I.

At 25° C., the mixture has a polarization of 38 nC/cm$^2$; a temperature dependence of the pitch is shown in the following table:

| T/°C. | 73 | 74 | 75 | 76 | 77 | 78 | 79 | 80 | 81 |
|---|---|---|---|---|---|---|---|---|---|
| Z/μm | +22 | +29 | +53 | >100 | ∞ | >100 | −42 | −32 | −25 |

The tetrahydrofuran derivatives can obviously be used, inter alia, for ferroelectric mixtures which, despite the very high polarization, have a very large pitch in the entire nematic phase region and can therefore be oriented well.

We claim:

1. A dopant for ferroelectric liquid-crystal mixtures, which comprises an optically active tetrahydrofuran-2-carboxylic acid ester of the general formula (I)

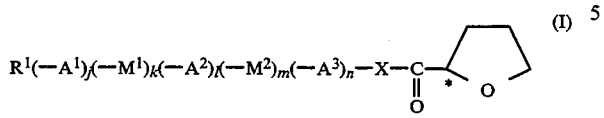

in which the symbols and indices have the following meaning:
* indicates an optically active carbon atom,
$R^1$ is

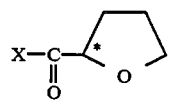

or a straight-chain or branched alkyl radical containing 1 to 16 carbon atoms or a straight-chain or branched alkenyl radical containing 3 to 16 carbon atoms, it being possible for these radicals themselves to contain asymmetric carbon atoms, for one or more non-adjacent —CH$_2$— groups to be replaced by —O—, —S—, —CO—, —O—CO— and/or —CO—O—, and for one or more hydrogen atoms to be replaced by fluorine, chlorine, bromine or CN, j and l are zero, 1 or 2,
k and m are zero or 1,
n is zero, 1 or 2,
with the following proviso: if j and/or l=zero, k=zero; if n=zero, m=zero; the sum of j+l+n is not less than 1 and not more than 3,
—$A^1$, —$A^2$ is

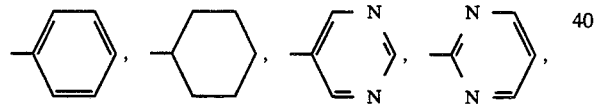

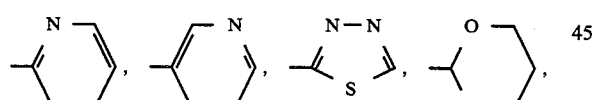

—$A^3$ is

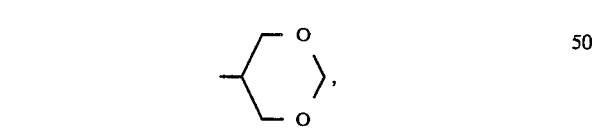

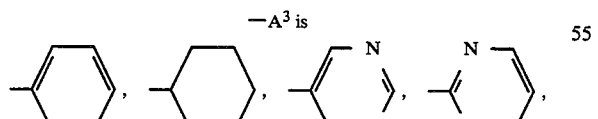

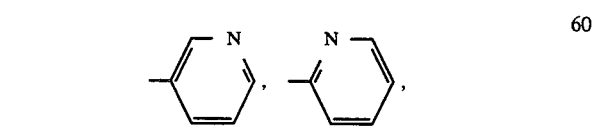

—$M^1$, —$M^2$ is —CO—O, —O—CO, —CH$_2$O, —OCH$_2$ and

X is O.

2. The dopant as claimed in claim 1, wherein the tetrahydrofuran-2-carboxylic acid ester is of the general formula (IV):

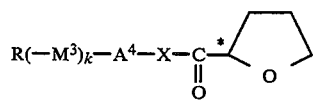

in which:
$R^4$ denotes a straight-chain or branched alkyl or alkenyl radical containing 6 to 12 carbon atoms, which may contain an asymmetric carbon atom;
—$M^3$ denotes —O, —S, —O—CO or —CO
—$A^4$ denotes

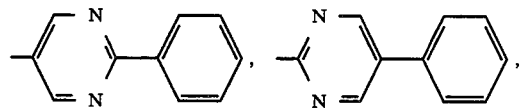

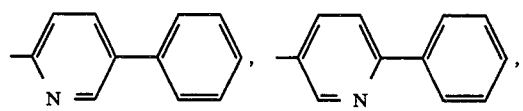

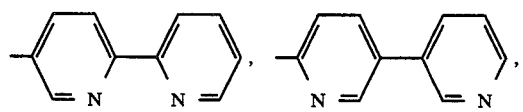

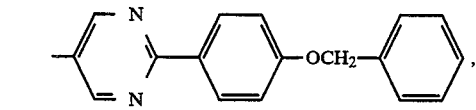

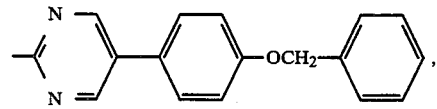

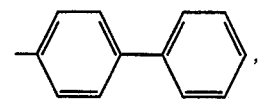

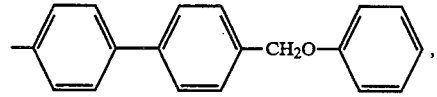

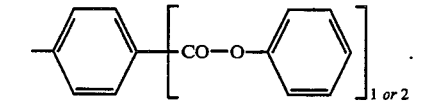

3. Liquid-crystal mixture which contains at least one optically active tetrahydrofuran-2-carboxylic acid ester of the general formula (I) as claimed in claim 1.

4. Liquid-crystal mixture which contains at least one optically active tetrahydrofuran-2-carboxylic acid ester of the general formula (IV) as claimed in claim 2.

5. Electro-optic switching or display component containing a liquid-crystal mixture as claimed in claim 3.

* * * * *